United States Patent [19]

Mason

[11] 4,268,285
[45] May 19, 1981

[54] AIR FRESHENING APPARATUS

[75] Inventor: Donald G. Mason, Park Ridge, Ill.

[73] Assignee: Mason Engineering & Designing Corporation, Rosemont, Ill.

[21] Appl. No.: 120,665

[22] Filed: Feb. 11, 1980

[51] Int. Cl.³ .............................................. B01D 19/00
[52] U.S. Cl. ........................................ 55/271; 55/473;
55/279; 422/4; 422/5; 422/124; 239/70; 261/99
[58] Field of Search ...................... 55/84, 97, 210, 244,
55/271, 274, 279, 467, 471–473, 500; 422/5.4,
123, 124; 98/115 LH; 261/99; 239/70, 34

[56] References Cited

U.S. PATENT DOCUMENTS

| | | | |
|---|---|---|---|
| 1,916,907 | 7/1933 | Sargent | 261/99 |
| 2,808,124 | 10/1957 | Attwood | 55/473 |
| 2,867,866 | 1/1959 | Steele | 422/124 |
| 3,298,674 | 1/1967 | Gilbertson | 422/4 |
| 3,301,167 | 1/1967 | Howard et al. | 55/DIG. 29 |
| 3,936,284 | 2/1976 | Mason | 55/274 |

FOREIGN PATENT DOCUMENTS 1125225  3/1962  Fed. Rep. of Germany ........ 239/74

Primary Examiner—Bernard Nozick
Attorney, Agent, or Firm—Lee & Smith

[57] ABSTRACT

The disclosed apparatus dispenses volatized air freshener compound into the room air forcibly moving the air through a prefilter and a high efficiency filter utilizing a fan disposed in the space therebetween. A container of volatile air freshener liquid or gel is positioned in a location such that the air drawn through the prefilter will pass across the top of the container. The container is provided with a lid mounted for movement to open and close the container, the lid being connected to and operable by a control such as a timing mechanism to adjustably regulate the amount of volatized air freshener compound which is permitted to escape into the air passing through the air filter, or the container can be kept totally closed and thus inoperative.

6 Claims, 7 Drawing Figures

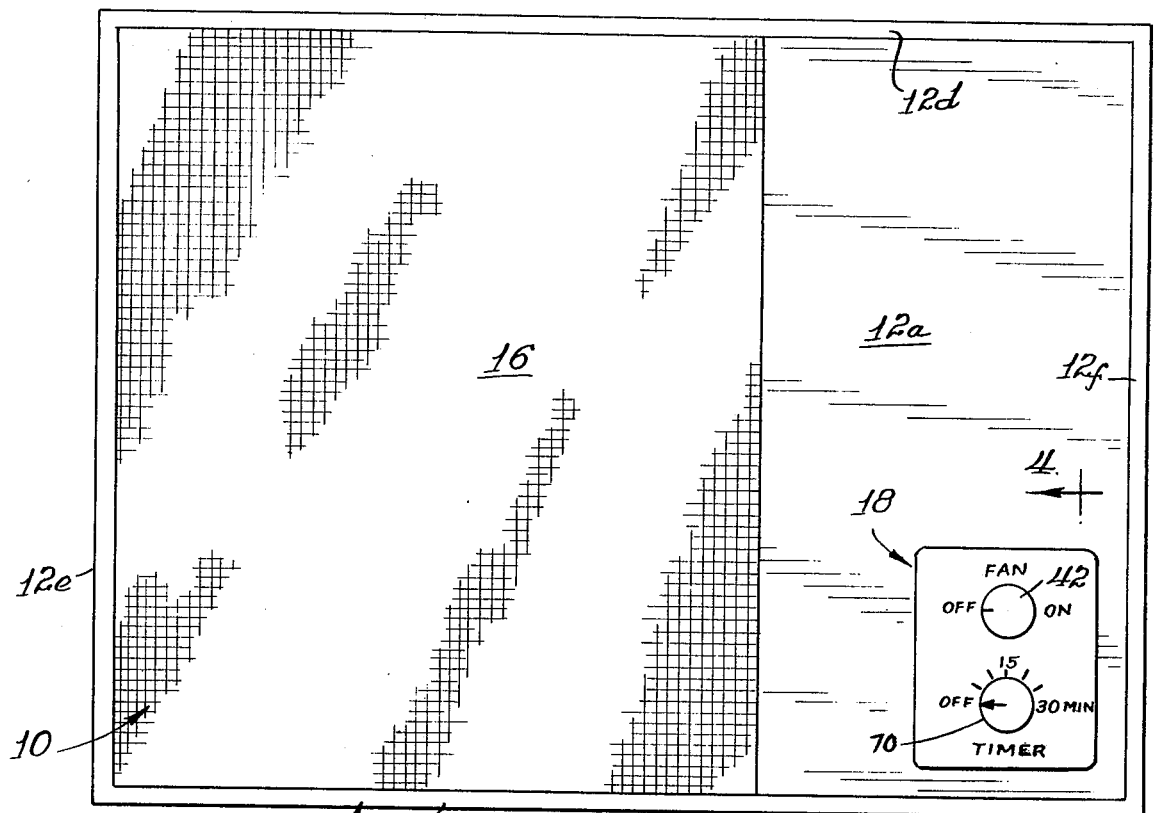
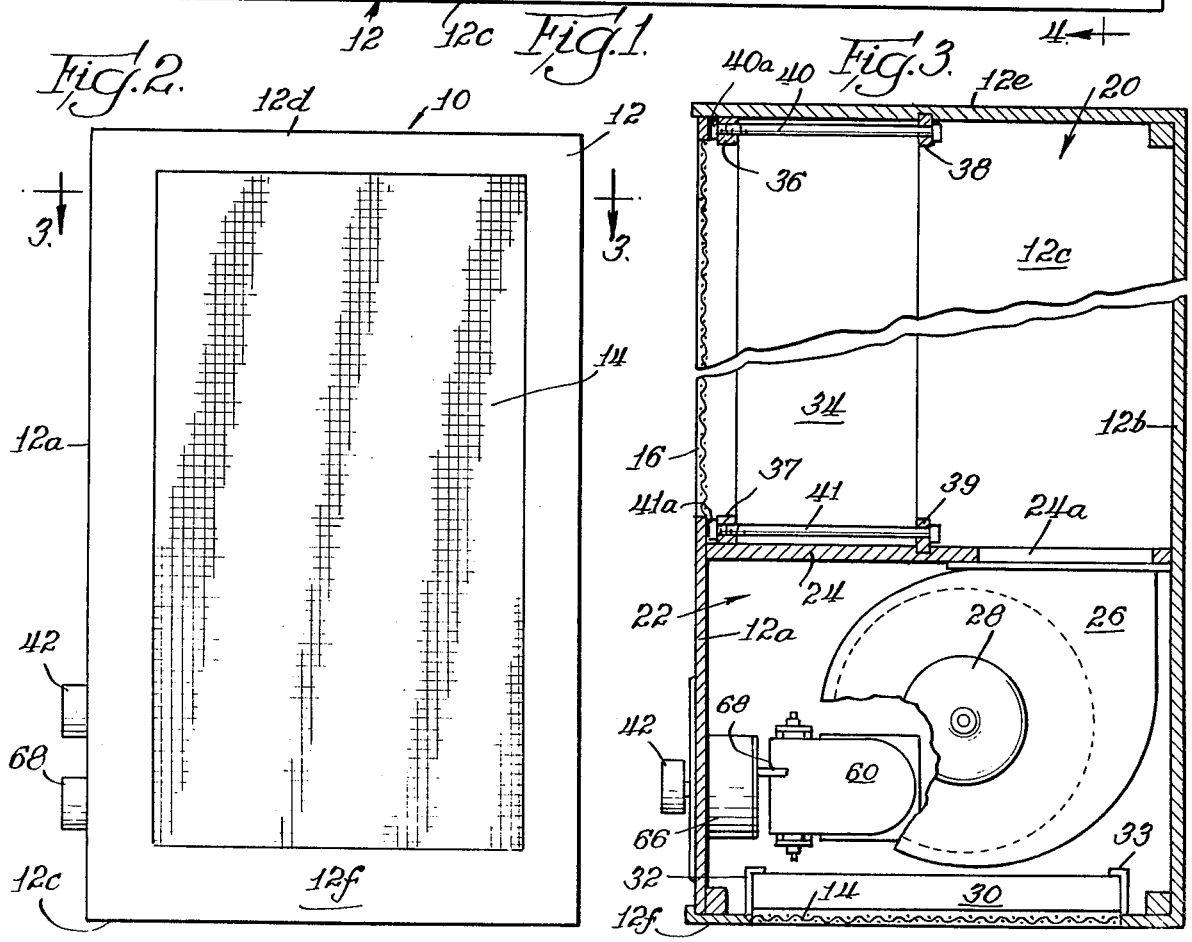

AIR FRESHENING APPARATUS

BACKGROUND OF THE INVENTION

This invention relates to a process and apparatus for dispensing a volatile air freshener into circulating room air, and more particularly to a process and apparatus for dispensing volatized air freshener compound into the air as the air is being filtered by an air filtering apparatus.

The invention is particularly adapted for use in connection with an air filtering apparatus of the type described in my U.S. Pat. No. 3,936,284 wherein air is drawn into a filter cabinet through a prefilter and is forced outwardly through a high efficiency HEPA type filter by means of the fan disposed in the space between these filters. Such an apparatus removes from the air such large particulates as street and house dust as well as sub-micronic size particulates such as tobacco smoke and typical airborne bacteria and viruses. The filter serves to remove by adsorption a wide variety of odors from the air being filtered. However, many odors which are caused by gases and particulates smaller than about 0.3 micron in size, may not be effectively removed by the filter apparatus. In order to treat the air containing odors originating from such sources, liquid malodor modifiers or air freshener chemicals have been employed. These are generally of two types: (a) those which mask odors, and (b) those which remove odors. Such air freshener chemicals are frequently used in households and are available in various familiar forms, including solids and liquids, with the liquid type being dispensed either by means of spraying or by means of a capillary wick which increases the surface area of contact between the liquid air freshener and the room air.

Heretofore, liquid air freshener chemicals have been added to the filtered air in an air filtering apparatus of the type illustrated in my U.S. Pat. No. 2,936,284. This has been done by positioning an open trough downstream from the high efficiency filter element, i.e., between that element and the exterior grid of the filter apparatus cabinet. The liquid air freshener was poured into this trough and was permitted to constantly evaporate into the filtered air as it flowed from the air filtering apparatus. Unfortunately, that arrangement provided no control over the amount of the air freshener that was being dispensed into the air, and as a result, either the liquid air freshener rapidly evaporated and the unit was operated without any air freshener, or an undesirable overabundance of the air freshener was dispensed into the air.

Another method previously used is the placement of an air freshener liquid or gel within the cabinet of the air filtering apparatus at the intake end. The air freshener was continuously volatilized into the air until the supply was exhausted or removed. Removal or closure of the container for the air freshener required turning the unit off and removing a section of the air filtering apparatus housing or enclosure in order to gain access to the air freshener.

These prior methods in reality provided no control over the dispensing of air freshener into the air.

One object of this invention is to provide a control over the dispensing of the air freshener into the air as it is flowing through the air filtering apparatus. The control provided by this invention (1) permits the air freshener dispensing to be adjusted from the exterior of the cabinet without requiring dismantling of any part of the cabinet and (2) provides an accurate means of varying the amount of air freshener media released into the room air. The control prevents the dispensing of air freshener when unnecessary and it permits the air freshener to be dispensed selectively in predetermined measured amounts depending upon the user's requirements. Thus, the air freshener liquid can be used much more economically and only in the quantities necessary to overcome the odors in the room.

It has been found that when the air freshener is dispensed by volatilization into the air upstream of the high efficiency or HEPA type filter, it serves not only to remove the odors from the air but it also tends to remove the odors from the upstream side of the filter. Over a period of several months the upstream side of the HEPA type filter traps particulates which are malodorous and to some extent the filter adsorbs malodorous gases. In previous application of air freshener chemicals to the air downstream of the HEPA type filter there was no effect upon the HEPA type filter itself. However, with the present invention the HEPA type filter may in effect be "cleansed" of these odors because the air carrying the air freshener will impinge upon the trapped particles and adsorb gases on the upstream side of the HEPA type filter.

SUMMARY OF THE INVENTION

In accordance with the invention, a process is provided for selectively dispensing volatilized air freshener compound into room air. This process includes the steps of forcibly moving the air through a prefilter and a high efficiency filter by means of a fan which is disposed in the space between these two filter elements. A container of volatile air freshener compound is positioned in this space, so that air which is drawn through the prefilter will pass across the container as it is moving to and through the high efficiency filter. The container has a lid positioned for operative engagement with an adjustable timing mechanism which may be set for selectively opening and closing the lid of the container in a preselected time sequence. In this way the dispensing of volatile air freshener into the air flowing through the space between the filter elements may be adjusted or it can be discontinued.

The air freshening apparatus of the invention is employed in combination with an air filtering apparatus having a cabinet, a filter media mounted with the cabinet, and a fan forcibly moving the air through the cabinet and the filter media. The improvement comprises a container of volatile air freshener compound means, such as a receiving frame, for positioning the container in a predetermined location within the interior of the cabinet in the path of the air being forcibly moved through the cabinet by the fan. A lid is provided for the container, and the lid is mounted, preferably on a mounting yoke, for movement between a first position wherein it covers the container and prevents the escape of volatilized air freshener compound into the air, and a second position wherein it uncovers the container to permit escape of the volatilized air freshener compound into the air. Control means, preferably in the form of a timing mechanism, is operable from the exterior of the cabinet for selectively moving the container lid between its first and second positions to adjustably regulate the escape of volatile air freshener into the air passing through the apparatus cabinet.

One feature of the invention is a particular mounting of the lid and its operation by means of a movable arm carried by the timer. The lid is preferably mounted at one side of the container positioning means for swinging movement about a horizontal pivotal axis. A portion of the lid extends outwardly to engage and sealingly close the container, and a second or operating portion is disposed on the other side of the pivotal axis for operative engagement with the arm on the timing mechanism so that when the timing mechanism is energized the arm will engage the operating portion of the lid and swing the container-engaging portion to an angularly elevated position out of contact with the container, thereby permitting the liquid air freshener within the container to volatilize into the air passing through the air filtering apparatus.

It is also preferred that within the container there be provided a capillary wick substantially the shape of the container, i.e., cylindrical, having its central area open, thereby presenting an annular cross-section. This wick not only causes the liquid air freshener to be drawn by capillary action to adjacent the top of the container for contact with the air, but it also increases the air-liquid surface contact area. Thus, the cylindrical wick increases the dispersion of the air freshener into the air during the time when the movable lid of the container is held in its open position by the timing mechanism.

BRIEF DESCRIPTION OF THE DRAWINGS

FIG. 1 is a front elevational view of an air filtering apparatus in which the air freshening process and apparatus of this invention may be embodied;

FIG. 2 is an end elevational view of the intake side of the air filtering apparatus of FIG. 1;

FIG. 3 is a sectional top plan view taken substantially along lines 3—3 of FIG. 2 and showing the interior of the air filtering apparatus, a portion of the fan having been broken away to show portions of the improved air freshening apparatus;

DETAILED DESCRIPTION OF THE PREFERRED EMBODIMENT

Figure 4:
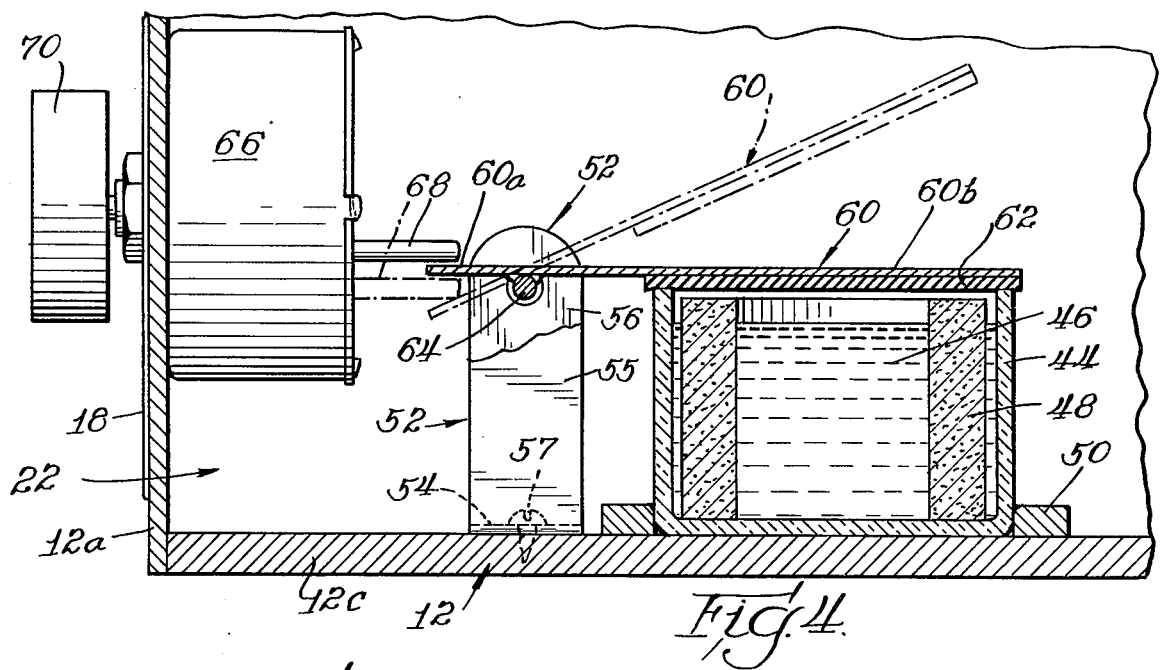
FIG. 4 is an enlarged cross-sectional view of a portion of the air filtering apparatus taken substantially along lines 4—4 of FIG. 1 and showing the details of the air freshening apparatus.

This invention is adapted to be used in conjunction with an air filtering apparatus of the type that is installed in a room and draws room air in through one side of the apparatus and exhausts clean filtered air out through another side of the apparatus. This type of air filtering apparatus is disclosed in U.S. Pat. No. 3,926,284 issued Feb. 3, 1976.

In FIGS. 1–3, there is illustrated an air filtering apparatus 10 having a cabinet 12. The cabinet has a front wall 12a, a rear wall 12b, a bottom wall 12c, a top wall 12d, and end walls 12e and 12f. In the cabinet end wall 12f is an opening covered by a removable grill 14 (see FIG. 2), through which room air is drawn into the cabinet of the air filtering apparatus. In the front wall 12a of the cabinet is another opening covered by a removable grill 16 through which the filtered air exits the apparatus. In some applications it may be desirable for the air to exit through an opening in the end wall 12e instead, rather than through the front wall opening as illustrated. A control panel 18, on the front wall 12a of the air filtering apparatus, carries manually operable controls which will be more fully hereinafter described.

The interior of the air filtering apparatus cabinet 12 is best illustrated in FIG. 3. The cabinet is divided into two chambers 20 and 22 by means of a partition 24 having an opening 24a. Except for the opening 24a, the two chambers 20 and 22 are sealed from each other by the partition 24. Mounted over the opening 24a of the partition 24, is a fan or blower 26 driven by an electric motor 28 mounted atop the blower. The blower 26 and the motor 28 are of standard well known construction but have a designed capability for forcing air through the dense, high efficiency filter. When the motor 28 is energized the blower will blow the air from the chamber 22 into the chamber 20 through the opening 24a in the partition. This results in pressure greater than ambient in chamber 22 and less than ambient in chamber 20.

The end grill 14 is removable providing access to a prefilter 30. The prefilter may consist of one or more elements or panels and is used to filter large particulates such as street and house dust and the like, which constitute approximately 90% by weight of all the particulates in the average indoor or outdoor air. This inexpensive filter may be constructed of spun fiberglass or other synthetic material of the type found in conventional furnace filters. It may be impregnated with a conventional sticky viscous substance which greatly increases efficiency. The prefilter element 30 may be held in place by means of suitable snap-fit or interference-fit channel brackets 32 and 33.

The front grill 16 of the apparatus is also removable, and mounted inwardly from this grill is a high efficiency or HEPA type filter element 34. This filter element is of the type developed by the U.S. Army Chemical Corp. and covered by Federal Standard 209 and Military Standard 282 (see also U.S. Pat. No. 3,498,032). This filter element may be a glass asbestos membrane having intimately distributed pores, capable of filtering out of the air passing therethrough, extremely large volumes of dust particles, sub-micronic in size, thus thoroughly cleansing the air. The HEPA type filter element 34 is located on one side of the chamber 20, preferably by means of clamping blocks 36 and 37, which clamp the filter 34 against inner brackets 38 and 39 by means of threaded rods 40 and 41 having nuts 40a and 41a respectively.

The motor 28 for the blower 26 is controlled by means of a suitable on/off control 42 operable from the front control panel 18 (see FIG. 1). When the control 42 is turned on, the fan 28 is actuated and the blower 26 draws air into the chamber 22 through the grill 14 and the prefilter 30. Air from chamber 22 is forced through the opening 24a in the partition 24 into the chamber 20 through the HEPA type filter 34 and outwardly through the front grill 16.

Figure 5:
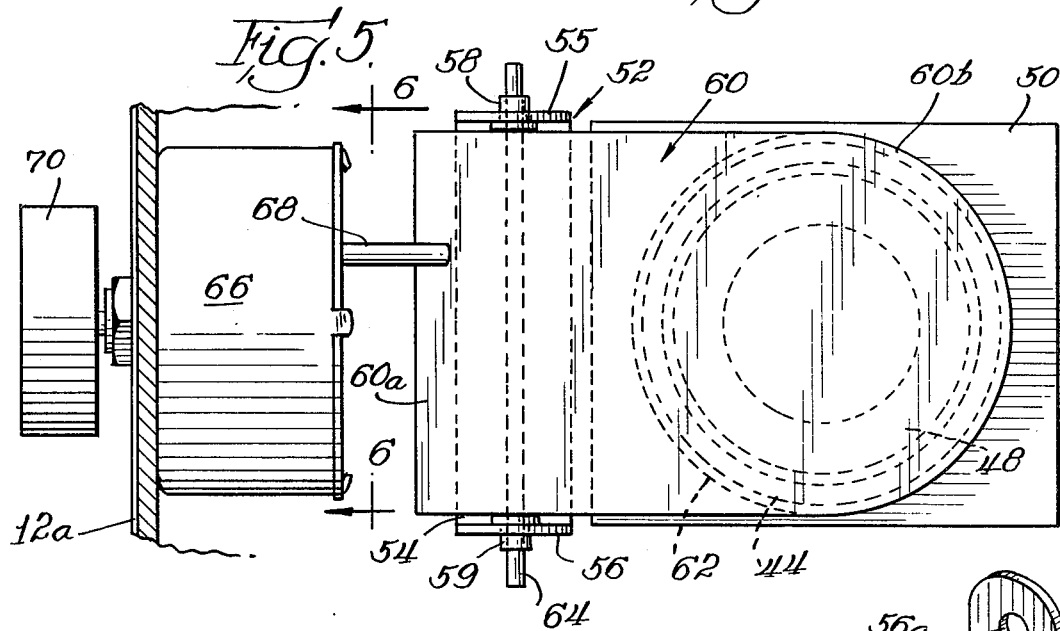
FIG. 5 is a top plan view of the portions of the air freshening apparatus illustrated in FIG. 4.
Figure 6:
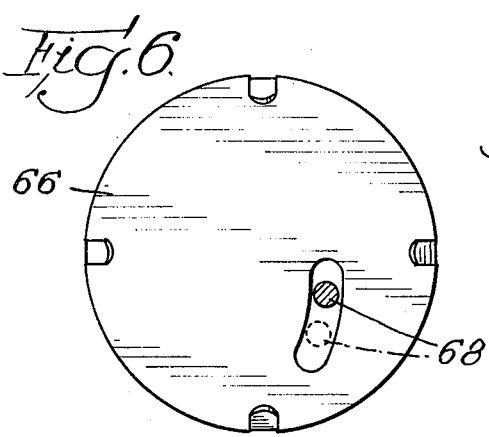
FIG. 6 is a cross-sectional elevational view of the air freshening apparatus taken substantially along lines 6—6 of FIG. 5.

Disposed within the first chamber 22, below the blower 26, is a container 44. This is best illustrated in FIGS. 4 and 5. The container is filled with a volatile liquid air freshener 46, and within the container is an absorbent wick 48 which extends from the bottom to adjacent the top of the container 44 and is thus, at least, partially immersed in the air freshener liquid 46. The wick is a tightly packed material having capillary size pores which draw the liquid 46 to the top of the container by capillary action.

The container 44 is open at the top, and means in the form of a receiving frame or guideway 50 positions the container in a predetermined location beneath the blower 26 within the interior of the cabinet chamber 22. The positioning is such that the container will be in the path of the air being forcibly drawn in through the prefilter 30 by the blower 26. The receiving frame 50 preferably completely encircles the bottom of the container 44 so that the container will be accurately positioned.

Figure 7:
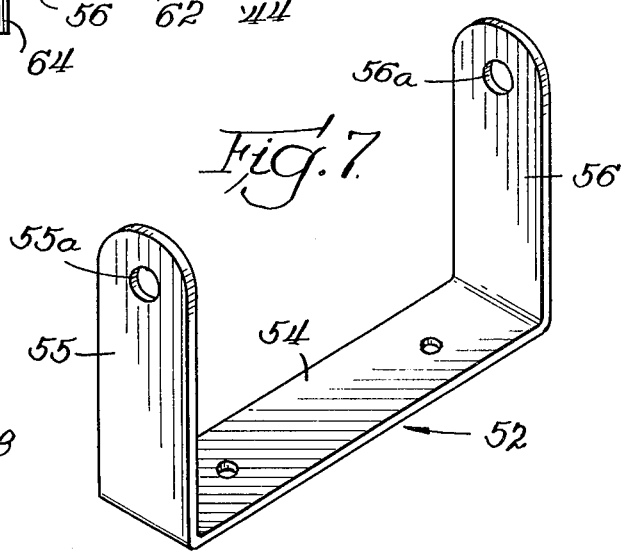
FIG. 7 is a perspective view of a portion of the air freshening apparatus.

Adjacent to the positioning frame 50 is a yoke-like mounting bracket 52 having a base 54 and a pair of upstanding arms 55 and 56, the upper ends of which are apertured at 55a and 56a, respectively. This mounting bracket is best illustrated in FIG. 7 and it is mounted in place by suitable threaded fasteners 57 (see FIG. 4). Mounted within the apertures 55a and 56a of the upstanding arms 55 and 56, respectively, are bearings 58 and 59. In order to close the top of the container 44, there is provided a cover plate or lid 60, preferably constructed of sheet metal and carrying on its underside a resilient sealing pad 62 which is slightly larger than the top of the container. The pad 62 is adapted to engage and seal the top edge of the container when the lid 60 is moved to its closed position as illustrated in full lines in FIG. 4. Affixed to the lid 60, by spot welding or other suitable means, is a pivot rod 64 which is journalled for horizontal pivotal movement within the bearings 58 and 59 carried by the mounting bracket arms 55 and 56. The pivot rod 64 is so positioned on the underside of the lid 60 that one portion 60a of the lid extends outwardly in one direction from the pivot rod and served as an operating arm, while the remaining portion 60b of the lid extends in the opposite direction over the container 44 and carries the container engaging and sealing pad 62. The lid 60 is pivotally movable with the pivot rod 64 between a first or horizontal position shown in solid lines in FIG. 4, and a second or angularly elevated position shown in dotted lines in FIG. 4. In the first or solid line position the sealing pad 62 on lid portion 60b sealingly engages and closes the container to prevent the escape of volatized liquid air freshener into the air flowing through the chamber 22. In the second or dotted line position the lid is raised to uncover the container and permit the escape of the volatized air freshener into the air flowing through the chamber 22.

It will be apparent that the positioning frame 50 cooperates with the lid 60 and its mounting to position the container 44 precisely in line with the lid, so that when the lid is lowered to its horizontal position the sealing pad 62 will properly engage and seal the top of the container preventing the evaporation or volatilization of the liquid air freshener from the container.

Control means 66 operable from the exterior of the air filtering apparatus cabinet 12 is provided for selectively moving the lid 60 between its open and closed positons, so that the escape of the volatized air freshener into the air passing through the cabinet may be adjustably regulated. This control means 66 is preferably a mechanical or electical timing device of common construction having a finger-like operating element or arm 68 extending outwardly for operative engagement with the operating portion 60a of the lid 60. The operating element 68 of the timing mechanism is movable between a raised or deenergized positon illustrated in solid lines in FIG. 4, and a lowered or energized position illustrated in dotted lines in FIG. 4.

When the timing mechanism 66 is turned on or energized the operating element 68 will be moved downwardly into engagement with the operating portion 60a of the lid 60, forcing the lid into its raised position illustrated in dotted lines in FIG. 4. After expiration of the preselected time interval for which the timer has been set, the timer will permit the operating element 68 to snap to its raised or solid line position in FIG. 4, permitting the lid 60 to again assume its horizontal container closing and sealing position illustrated in solid lines.

In the illustrated embodiment, the timer is a simple mechanical timer of conventional construction, operated by means of a control knob 70 which extends through the control panel 18 on the front of the air filtering apparatus. The timing mechanism is preferably so calibrated that when the control knob 70 has been turned approximately 180° the timer will operate for about 30 minutes. The particular mechanical timer illustrated is manufactured by M. H. Rhodes, Inc., of Avon, Connecticut, and the operating arm 68 of that timer moves about ¼ of an inch between its energized and deenergized positions.

The fan motor control 42 and the air freshener lid control means (timing mechanism) 66 may be operated electrically or even remotely, if desired. The timing mechanism 66 may be designed for pre-selection of operating times over a 24 hour period, if desired.

In operation, the fan 26 is turned on by means of the control knob 42 on the control panel 18, causing room air to be drawn in through the end grill 14 and prefilter 30 into the chamber 22. As the air moves through the filter 30 and into the intake of the blower 26 it will move across the top of the container 44 containing the volatile liquid air freshener. If the control or timing mechanism 66 is deenergized, the lid 60 will cover the container 44 and prevent the volatilization of the liquid air freshener into the air in the chamber 22. However, if the control timing mechanism is energized by rotating the control knob 70 to the desired setting, the operating element 68 will be lowered and the lid 60 will be swung to its raised position, illustrated in dotted lines in FIG. 4. When the lid 60 is in this position the air passing from the prefilter 30 to the blower 26 will move across the open container so that the liquid will be volatilized from the container wick 48 into the moving air. The air laden with the volatilized (gaseous) air freshener will than be forced into the second chamber 20 and then outwardly through the HEPA type filter 34 and the front grill 16. Since the air freshener enters the air as a volatilized liquid, i.e., a gas, it will pass readily through the HEPA filter 44 although some will impinge upon the filter and thus serve to not only deodorize the room air passing through the air filtering apparatus, but it will also tend to deodorize the particles and adsorbed gases which have been trapped in the HEPA type filter 34.

The amount of the air freshener which is volatilized into the air moving through the air filtering apparatus will be dependent upon the setting of the knob 66 for the control timing mechanism 66.

Thus, the process for dispensing the volatile air freshener into the room includes the steps of forcibly moving the air through a prefilter 30 and a high efficiency filter 34 by means of a fan or blower 26 disposed in the space between these two filter elements. A container of volatile air freshener compound is positioned in the space such that air is drawn across the container as it moves from the prefilter to the high efficiency filter, and the container has a lid positioned for operative engagement with an adjustable timing mechanism which may be adjustably set for opening and closing the lid on the container in a preselected time sequence, thereby regulating the amount of the volatile air freshener dispensed into the air flowing through the space.

It will be understood that the foregoing description has been given only by way of example and that various changes and modifications to the apparatus may be undertaken without departing from the spirit and scope of the invention as defined by the appended claims.

What is claimed is:

1. In combination with an air filtering apparatus having a cabinet, means for filtering the air as it is moved through said cabinet, and a fan for forcibly moving air through the cabinet and filtering means; the improvement comprising a container of volatile air freshener, means for positioning said container in a predetermined location within the interior of said cabinet in the path of the air being forcibly moved therethrough by said fan, a lid for said container mounted at one side of said container positioning means for swinging movement about a pivotal axis between a first position covering said container to prevent the escape of the volatile air freshener into the air and a second position uncovering the container to permit the escape of the volatile air freshener into the air, and control means including a timer operable from the exterior of said cabinet and selectively energizable for a preselected variable period of time, said timer having an element positioned for operative engagement with said lid, said timer element when said timer is deenergized being in a first position to permit said lid to rest in its first position covering said container, said element being movable to a second position when said timer is energized to effect corresponding movement of said lid to its second position, whereby the escape of volatile air freshener into the air passing through the cabinet may be adjustably regulated in accordance with the setting of said timer.

2. The structure of claim 1 in which the pivotal axis of said lid mounting is horizontal.

3. The structure of claim 1 wherein the air freshener is a liquid and said container has a wick, the upper end of which extends to the upper end of said container, said wick being effective for drawing the air freshener liquid by capillary action to adjacent the top of said container.

4. The structure of claim 3 wherein said wick is substantially the shape of the interior of the container having its central area open and its outer surface spaced inwardly from the inner surface of said container.

5. The structure of claim 4 wherein said container and said wick are substantially cylindrical.

6. In combination with an air filtering apparatus having a cabinet, a prefilter and a high efficiency filter disposed in spaced relationship within said cabinet, partition means dividing the space between said filters into separate prefilter and high efficiency filter compartments and a fan associated with said partition means for forcibly moving air through said partition means from said prefilter through said high efficiency filter and the associated compartments adjacent said filters; the improvement comprising a container of volatile air freshener, means for positioning said container in a predetermined location within said compartment adjacent said prefilter in the path of the air being forcibly moved therethrough by said fan, a lid for said container mounted at one side of said container positioning means for swinging movement about a pivotal axis between a first position covering said container to prevent the escape of the volatile air freshener into the air and a second position uncovering the container to permit the escape of the volatile air freshener into the air, and control means including a timer operable from the exterior of said cabintet and selectively energizable for a preselected variable period of time, said timer having an element positioned for operative engagement with said lid, said timer element when said timer is deenergized being in a first position to permit said lid to rest in its first position covering said container, said element being movable to a second position when said timer is energized to effect corresponding movement of said lid to its second position, whereby the escape of volatile air freshener into the air passing tyhrough the cabinet may be adjustably regulated in accordance with the setting of said timer.

* * * * *